US012558100B2

(12) United States Patent
Dahan et al.

(10) Patent No.: US 12,558,100 B2
(45) Date of Patent: Feb. 24, 2026

(54) INTRAVASCULAR DEVICE FOR ANCHORING A GRAFT TO TISSUE

(71) Applicant: Endoron Medical Ltd., Kfar Saba (IL)

(72) Inventors: Nir D. Dahan, Jerusalem (IL); Eyal Teichman, Hod HaSharon (IL); Tanhum Feld, Moshav Merhavia (IL)

(73) Assignee: Endoron Medical Ltd., Kfar Saba (IL)

( * ) Notice: Subject to any disclaimer, the term of this patent is extended or adjusted under 35 U.S.C. 154(b) by 0 days.

(21) Appl. No.: 18/679,141

(22) Filed: May 30, 2024

(65) Prior Publication Data

US 2024/0398420 A1 Dec. 5, 2024

Related U.S. Application Data

(60) Provisional application No. 63/470,470, filed on Jun. 2, 2023.

(51) Int. Cl.
*A61B 17/12* (2006.01)
(52) U.S. Cl.
CPC .. *A61B 17/12172* (2013.01); *A61B 17/12109* (2013.01); *A61B 17/12136* (2013.01); *A61B 2017/1205* (2013.01)
(58) Field of Classification Search
CPC ........ A61B 17/12172; A61B 17/12109; A61B 17/12136; A61B 2017/1205; A61F 2002/825
See application file for complete search history.

(56) References Cited

U.S. PATENT DOCUMENTS

| | | | |
|---|---|---|---|
| 4,586,923 A | 5/1986 | Gould et al. | |
| 4,747,899 A | 5/1988 | Hasegawa | |
| 5,151,105 A | 9/1992 | Kwan-Gett | |
| 5,195,968 A | 3/1993 | Lundquist et al. | |
| 5,207,695 A | 5/1993 | Trout, III | |

(Continued)

FOREIGN PATENT DOCUMENTS

| | | |
|---|---|---|
| CN | 101394815 A | 3/2009 |
| CN | 104055604 A | 9/2014 |

(Continued)

OTHER PUBLICATIONS

Extended European Search Report for European Application No. 19819405.2, mailed Feb. 14, 2022, 9 Pages.

(Continued)

*Primary Examiner* — Katherine M Shi
*Assistant Examiner* — Mohammed S Adam
(74) *Attorney, Agent, or Firm* — Greenberg Traurig, LLP; Christopher C. Bolten; Albert K. Heng

(57) ABSTRACT

Tissue anchoring devices including a radially expandable frame having a plurality of longitudinal struts and a plurality of deployable anchors configured to penetrate a stent graft and tissue, and systems for delivering and deploying the tissue anchoring devices at a target location are provided. The adjacent longitudinal struts are interconnected by a plurality of expandable struts, and a ring of these expandable struts may be angled radially outward relative to a remainder of the expandable struts in an expanded configuration. Each of the plurality of anchors may include one or more anti-buckling mechanisms to facilitate penetration into the graft/tissue.

29 Claims, 12 Drawing Sheets

(56) References Cited

U.S. PATENT DOCUMENTS

| | | | |
|---|---|---|---|
| 5,415,664 | A | 5/1995 | Pinchuk |
| 5,700,119 | A | 12/1997 | Wakai |
| 5,906,590 | A | 5/1999 | Hunjan et al. |
| 6,053,943 | A | 4/2000 | Edwin et al. |
| 6,551,302 | B1 | 4/2003 | Rosinko et al. |
| 6,592,593 | B1 | 7/2003 | Parodi et al. |
| 6,767,359 | B2 | 7/2004 | Weadock |
| 6,800,081 | B2 | 10/2004 | Parodi |
| 6,960,217 | B2 | 11/2005 | Bolduc |
| 7,025,779 | B2 | 4/2006 | Elliott |
| 7,128,754 | B2 | 10/2006 | Bolduc |
| 7,267,685 | B2 | 9/2007 | Butaric et al. |
| 7,326,231 | B2 | 2/2008 | Phillips et al. |
| 7,491,232 | B2 | 2/2009 | Bolduc et al. |
| 7,544,198 | B2 | 6/2009 | Parodi |
| 7,637,932 | B2 | 12/2009 | Bolduc et al. |
| 7,682,390 | B2 | 3/2010 | Seguin |
| 7,959,663 | B2 | 6/2011 | Bolduc |
| 7,959,670 | B2 | 6/2011 | Bolduc |
| 8,075,570 | B2 | 12/2011 | Bolduc et al. |
| 8,083,752 | B2 | 12/2011 | Bolduc |
| 8,092,519 | B2 | 1/2012 | Bolduc |
| 8,157,146 | B2 | 4/2012 | Edoga et al. |
| 8,231,639 | B2 | 7/2012 | Bolduc et al. |
| 8,685,044 | B2 | 4/2014 | Bolduc et al. |
| 8,690,897 | B2 | 4/2014 | Bolduc |
| 9,241,710 | B2 | 1/2016 | Paz et al. |
| 9,320,503 | B2 | 4/2016 | Bolduc |
| 9,320,589 | B2 | 4/2016 | Bolduc |
| 9,320,591 | B2 | 4/2016 | Bolduc |
| 9,730,790 | B2 | 8/2017 | Quadri et al. |
| 9,808,250 | B2 | 11/2017 | Bolduc et al. |
| 9,848,869 | B2 | 12/2017 | Bolduc et al. |
| 9,867,611 | B2 | 1/2018 | Smith et al. |
| 9,968,353 | B2 | 5/2018 | Bolduc et al. |
| 9,974,671 | B2 | 5/2018 | Bolduc et al. |
| 10,194,905 | B2 | 2/2019 | Bolduc et al. |
| 10,299,791 | B2 | 5/2019 | Bolduc |
| 10,357,230 | B2 | 7/2019 | Bolduc |
| 10,595,867 | B2 | 3/2020 | Bolduc et al. |
| 11,103,341 | B2 | 8/2021 | Arbefeuille et al. |
| 11,896,509 | B2 | 2/2024 | Teichman et al. |
| 12,097,136 | B2 | 9/2024 | Karmeli et al. |
| 12,295,868 | B2 | 5/2025 | Karmeli et al. |
| 2003/0220683 | A1 | 11/2003 | Minasian et al. |
| 2005/0033398 | A1 | 2/2005 | Seguin |
| 2005/0085897 | A1 | 4/2005 | Bonsignore |
| 2005/0096731 | A1 | 5/2005 | Looi et al. |
| 2009/0048665 | A1 | 2/2009 | Miron et al. |
| 2011/0106148 | A1 | 5/2011 | Ginn et al. |
| 2012/0130470 | A1 | 5/2012 | Agnew et al. |
| 2012/0143317 | A1* | 6/2012 | Cam ......................... A61F 2/90 |
| | | | 623/1.35 |
| 2012/0172968 | A1 | 7/2012 | Chuter et al. |
| 2013/0023981 | A1 | 1/2013 | Dierking et al. |
| 2013/0172983 | A1 | 7/2013 | Clerc et al. |
| 2015/0018933 | A1 | 1/2015 | Yang et al. |
| 2015/0148896 | A1* | 5/2015 | Karapetian ............... A61F 2/88 |
| | | | 623/2.11 |
| 2015/0335861 | A1 | 11/2015 | Osypka et al. |
| 2017/0056174 | A1 | 3/2017 | Tobis et al. |
| 2017/0189179 | A1* | 7/2017 | Ratz ...................... A61F 2/2418 |
| 2017/0333029 | A1 | 11/2017 | O'Hara et al. |
| 2018/0014956 | A1 | 1/2018 | Horgan et al. |
| 2018/0036111 | A1 | 2/2018 | Despalle De Béarn |
| 2018/0049873 | A1 | 2/2018 | Manash et al. |
| 2018/0116798 | A1 | 5/2018 | Perszyk |
| 2018/0116843 | A1 | 5/2018 | Schreck et al. |
| 2018/0206975 | A1* | 7/2018 | Shalev ................... A61F 2/954 |
| 2018/0289476 | A1 | 10/2018 | Vyas et al. |
| 2019/0015633 | A1 | 1/2019 | Bednarek et al. |
| 2020/0086084 | A1 | 3/2020 | Sapir et al. |
| 2020/0390549 | A1 | 12/2020 | Marchand et al. |
| 2020/0405515 | A1 | 12/2020 | Labrecque et al. |
| 2021/0093313 | A1 | 4/2021 | Karmeli et al. |
| 2022/0331133 | A1 | 10/2022 | Teichman et al. |
| 2024/0374867 | A1 | 11/2024 | Teichman |
| 2025/0281313 | A1 | 9/2025 | Karmeli et al. |

FOREIGN PATENT DOCUMENTS

| | | | |
|---|---|---|---|
| CN | 107530166 | A | 1/2018 |
| EP | 2008616 | A1 | 12/2008 |
| EP | 3167850 | A1 | 5/2017 |
| JP | 2005525910 | A | 9/2005 |
| JP | 2008029839 | A | 2/2008 |
| JP | 2009528113 | A | 8/2009 |
| JP | 2009233201 | A | 10/2009 |
| WO | WO-2007099448 | A2 | 9/2007 |
| WO | WO-2019239409 | A1 | 12/2019 |
| WO | WO-2021240411 | A1 | 12/2021 |
| WO | WO-2022064492 | A1 | 3/2022 |
| WO | WO-2023058023 | A1 | 4/2023 |

OTHER PUBLICATIONS

International Search Report and Written Opinion for International Application No. PCT/IL2019/050664, mailed Oct. 3, 2019, 10 Pages.

International Search Report and Written Opinion for International Application No. PCT/IL2021/051152, mailed Mar. 1, 2022, 12 Pages.

International Search Report and Written Opinion for International Application No. PCT/IL2022/051058, mailed Feb. 17, 2023, 8 Pages.

Supplementary European Search Report and the European Search Opinion for European Re. Application No. 19819405.2, mailed Mar. 3, 2022, 1 Page.

Invitation to Pay Additional Fees and Partial Search Report dated Sep. 13, 2024 in Int'l PCT Patent Appl. Serial No. PCT/IB2024/055321.

Berezowski, et al., Inaccurate aortic stent graft deployment in the distal landing zone: incidence, reasons and consequences, European Journal of Cardio-Thoracic Surgery, 53(6):1158-1164 (Jun. 2018).

International Search Report and Written Opinion dated Nov. 5, 2024 in Int'l PCT Patent Appl. Serial No. PCT/IB2024/055321.

International Search Report & Written Opinion dated Nov. 5, 2024 in Int'l PCT Patent Appl. Serial No. PCT/IB2024/055321.

EP Extended Search Report dated May 30, 2025, in EP Patent Application Serial No. 22878086.2.

* cited by examiner

INTRAVASCULAR DEVICE FOR ANCHORING A GRAFT TO TISSUE

CROSS-REFERENCE TO RELATED APPLICATIONS

This application claims priority to U.S. Provisional Patent Application No. 63/470,470, filed Jun. 2, 2023, the entire contents which are incorporated herein by reference.

FIELD OF THE INVENTION

The present technology relates to a tissue anchoring device and to a method and system for using same. Embodiments of the present invention relate to an expandable frame carrying deployable struts for stabilizing the device during delivery and deployable tissue anchors for anchoring an endoluminal device such as a stent graft to a tissue such as vascular tissue.

BACKGROUND

Over the past decades minimally invasive procedures have gradually replaced open procedures in treatment of various pathologies. One example of such a pathology is vascular aneurysm, a condition characterized by abnormal dilation of a blood vessel that typically results from weakening of an arterial wall caused by disease or genetic predisposition.

Aneurysms have been commonly treated by open surgical procedures in which the diseased vessel segment is bypassed or externally covered with a protective graft. Such an open procedure has been replaced by a minimally invasive procedure in which a stent graft including a metallic support structure carrying a graft material such as Dacron, or polytetrafluoroethylene (PTFE) is positioned within the diseased vessel using a delivery catheter introduced through a vascular access site. Although effective in sealing off the aneurysm, stent grafts can migrate over time due to the force associated with the blood flowing through the stent graft and the expansion and contraction of the arteries due to the pulsation of blood therethrough. Such migration can lead to leakage of blood into the aneurysm site.

Anchors for tissue fixation and stents carrying such anchors have been developed in order to prevent stent graft migration. However, such solutions have not fully addressed the problem of migration due to the limited vessel wall area for fixation above an aneurysm and poor tissue fixation capabilities of such anchors. Another limitation of stent grafts is mispositioning during delivery. Stent grafts can shift during delivery resulting in less-than-optimal coverage of the aneurysm and, depending on the aneurysm, unwanted partial blockage of branching arteries.

In view of the foregoing drawbacks of previously known systems and methods, there is a need for, and it would be highly advantageous to have, a tissue anchoring device that can be used to anchor a stent graft to a vessel wall devoid of the above limitations.

SUMMARY

The present disclosure overcomes the drawbacks of previously-known systems and methods by providing a tissue anchoring device comprising a radially expandable frame configured to transition between a collapsed configuration and an expanded configuration. The frame may comprise a plurality of longitudinal struts interconnected by a plurality of expandable struts. Accordingly, in the expanded configuration, a ring of expandable struts of the plurality of expandable struts may be angled radially outward relative to a remainder of the plurality of expandable struts. Each of the plurality of expandable struts interconnecting adjacent longitudinal struts may be configured to expand circumferentially from a V shape in the collapsed configuration to a dome shape in the expanded configuration. Further, a peak of one or more expandable struts of the ring of expandable struts may comprise an eyelet.

Moreover, the ring of expandable struts of the plurality of expandable struts may be configured to contact a wall of a biological vessel prior to the remainder of the plurality of expandable struts as the frame transitions from the collapsed configuration to the expanded configuration within the biological vessel. In some embodiments, the ring of expandable struts of the plurality of expandable struts may be disposed between distal-most expandable struts of the plurality of expandable struts and proximal-most expandable struts of the plurality of expandable struts. In addition, at least a portion of at least one longitudinal strut of the plurality of longitudinal struts may comprise an S shape. The at least one longitudinal strut of the plurality of longitudinal struts may be disposed between the ring of expandable struts of the plurality of expandable struts and distal-most expandable struts of the plurality of expandable struts. In addition, a proximal end of each of the plurality of longitudinal struts may comprise an eyelet. In some embodiments, the plurality of longitudinal struts may comprise six longitudinal struts, and the plurality of expandable struts may comprise eighteen expandable struts.

Distal expandable struts of the plurality of expandable struts may each comprise an anchor having a tissue penetrating portion. The tissue penetrating portion of each anchor may be configured to penetrate a graft disposed within the biological vessel and at least an inner wall of the biological vessel. Moreover, each anchor may be attached to each of the distal expandable struts via a support frame. Further, each anchor may comprise at least two prongs configured to transition between a restrained state where the at least two prongs are juxtaposed and an unrestrained state where the at least two prongs are deflected away from each other. Additionally, each anchor may comprise a sleeve slidably disposed over the at least two prongs. The sleeve may be configured to move from a first position where the at least two prongs are in the restrained state and a second position where the at least two prongs are permitted to transition to the unrestrained state. In addition, each anchor may comprise a distal stop configured to prevent movement of the sleeve distally beyond the distal stop, and a proximal stop configured to prevent movement of the sleeve proximally beyond the proximal stop. Accordingly, upon application of at least a predetermined force to the sleeve, the anchor may be configured to contract inward to permit the sleeve to move proximally beyond the proximal stop.

In some embodiments, the at least two prongs may comprise two external prongs and two internal prongs. For example, in the unrestrained state, a first pair of external and internal prongs may be configured to deflect away from a second pair of external and internal prongs. At least one pair of juxtaposed prongs of the at least two prongs may comprise a buckling prevention lock. For example, the buckling prevention lock may comprise a protrusion extending from a first prong of the at least one pair of juxtaposed prongs, and a recess formed in a second prong of the at least one pair of juxtaposed prongs. Accordingly, in the restrained state, the recess may be configured to receive the protrusion therein to provide friction and prevent buckling of the anchor as the at least one pair of juxtaposed prongs transitions from the restrained state to the unrestrained state. The buckling prevention lock may be disposed on a middle region of the at least one pair of juxtaposed prongs. In some embodiments, the at least one pair of juxtaposed prongs may comprise the two internal prongs. Additionally, or alternatively, the at least one pair of juxtaposed prongs may comprise at least one of the first pair of external and internal prongs or the second pair of external and internal prongs.

In accordance with another aspect of the present disclosure, a system for delivering and deploying a tissue anchoring device within a biological vessel is provided. The system may comprise a dual balloon catheter comprising an elongated shaft, a locking balloon disposed on a distal region of the elongated shaft, and an activation balloon disposed on the distal region of the elongated shaft distal to the locking balloon. The inflatable locking balloon may be configured to be inflated to contact at least a proximal portion of the tissue anchoring device prevent movement of the tissue anchoring device relative to the biological vessel, and the activation balloon may be configured to be inflated to apply a radially outward force to expand at least a distal portion of the tissue anchoring device and cause one or more anchors of the tissue anchoring device to penetrate the biological vessel. Moreover, a distal end of the locking balloon may be coupled to the elongated shaft in a manner such that, when the locking balloon is inflated, a distal portion of the locking balloon is inverted within itself.

The activation balloon may comprise a foldable internal balloon and an expandable outer sleeve disposed over the foldable internal balloon. The expandable outer sleeve may be configured to prevent puncturing of the foldable internal balloon as the foldable internal balloon is inflated within the biological vessel. The system further may comprise a delivery catheter comprising an elongated shaft having a distal end comprising a nose cone, a retractable sheath configured to releasably engage the nose cone, the sheath configured to receive the tissue anchoring device therein in a collapsed state, and a holder slidably disposed within the sheath, the holder comprising a plurality of recesses configured to releasably engage a plurality of eyelets disposed on the proximal portion of the tissue anchoring device. Accordingly, movement of the nose cone distally relative to the sheath may expose the distal portion of the tissue anchoring device, such that the distal portion of the tissue anchoring device transitions from the collapsed state to a partially expanded state. Moreover, movement of the sheath proximally relative to the nose cone may expose the proximal portion of the tissue anchoring device, such that the proximal portion of the tissue anchoring device transitions from the collapsed state to a fully expanded state.

In accordance with another aspect of the present disclosure, a method of securing a graft to a tissue is provided. The method may comprise: collapsing a tissue anchoring device within a delivery catheter, the tissue anchoring device comprising a radially expandable frame configured to transition between a collapsed configuration and an expanded configuration, the frame comprising a plurality of longitudinal struts interconnected by a plurality of expandable struts, a ring of expandable struts of the plurality of expandable struts angled radially outward relative to a remainder of the plurality of expandable struts in the expanded configuration; partially releasing the tissue anchoring device from the delivery catheter in a vessel such that the ring of expandable struts of the plurality of expandable struts contacts a graft positioned within the vessel to thereby stabilize the frame within the graft; fully releasing the tissue anchoring device from the delivery catheter; and removing the delivery catheter from the vessel.

Distal expandable struts of the plurality of expandable struts may each comprise an anchor having a tissue penetrating portion. Accordingly, the method further may comprise driving the tissue penetrating portion of each anchor through the graft and the vessel. For example, driving the tissue penetrating portion of each anchor through the graft and the vessel may comprise inflating an activation balloon of a balloon catheter within at least a distal portion of the tissue anchoring device. Thus, the method further may comprise inflating a locking balloon of the balloon catheter within at least a proximal portion of the tissue anchoring device to secure the tissue anchoring device within the vessel during inflation of the activation balloon. The locking balloon may be proximal to the activation balloon.

In accordance with another aspect of the present disclosure, a tissue anchoring device is provided. The tissue anchoring device may include a radially expandable frame comprising a plurality of longitudinal struts interconnected by a plurality of expandable struts, and a plurality of anchors disposed on distal expandable struts of the plurality of expandable struts. Each anchor may comprise at least two prongs configured to transition between a restrained state where the at least two prongs are juxtaposed and an unrestrained state where the at least two prongs are deflected away from each other. Moreover, at least one pair of juxtaposed prongs of the at least two prongs may comprise a buckling prevention lock disposed on a middle region of the at least one pair of juxtaposed prongs. Additionally, each anchor may comprise a tissue penetrating portion configured to penetrate a graft disposed within the biological vessel and at least an inner wall of the biological vessel. Further, each anchor may be attached to each of the distal expandable struts via a support frame.

In addition, each anchor may comprise a sleeve slidably disposed over the at least two prongs. The sleeve may be configured to move from a first position where the at least two prongs are in the restrained state and a second position where the at least two prongs are permitted to transition to the unrestrained state. The buckling prevention lock may be disposed on the middle region of the at least one pair of juxtaposed prongs between the first position of the sleeve and a base of the anchor. Moreover, each anchor may comprise a distal stop configured to prevent movement of the sleeve distally beyond the distal stop, and a proximal stop configured to prevent movement of the sleeve proximally beyond the proximal stop. Accordingly, upon application of at least a predetermined force to the sleeve, the anchor may be configured to contract inward to permit the sleeve to move proximally beyond the proximal stop.

In some embodiments, the at least two prongs may comprise two external prongs and two internal prongs. For example, the at least one pair of juxtaposed prongs may comprise the two internal prongs. In the unrestrained state, a first pair of external and internal prongs may be configured to deflect away from a second pair of external and internal prongs. The at least one pair of juxtaposed prongs may comprise at least one of the first pair of external and internal prongs or the second pair of external and internal prongs. Moreover, the buckling prevention lock may comprise a protrusion extending from a first prong of the at least one pair of juxtaposed prongs, and a recess formed in a second prong of the at least one pair of juxtaposed prongs. Accordingly, in the restrained state, the recess may be configured to receive the protrusion therein to provide friction and prevent buckling of the anchor as the at least one pair of juxtaposed prongs transitions from the restrained state to the unrestrained state.

According to one aspect of the present disclosure there is provided a tissue anchoring device comprising a radially expandable frame having a plurality of longitudinal struts, wherein adjacent longitudinal struts are interconnected by a plurality of expandable struts and further wherein one of the plurality of expandable struts is angled radially outward from a remainder of the plurality of expandable struts.

According to embodiments of the present disclosure each of the plurality of expandable struts expands circumferentially from a V shape to a dome shape when the radially expandable frame radially expands.

According to embodiments of the present disclosure one of the plurality of expandable struts includes an eyelet at a tip of the dome.

According to embodiments of the present disclosure a proximal end of each of the longitudinal struts includes an eyelet.

According to embodiments of the present disclosure distal expandable struts of the plurality of expandable struts each include an anchor having a tissue penetrating portion.

According to embodiments of the present disclosure the anchor is attached to each of the distal expandable struts via a support frame.

According to embodiments of the present disclosure one of the plurality of expandable struts contacts a wall of a biological vessel prior to the remainder of the plurality of expandable struts when the radially expandable frame is radially expanded within the biological vessel.

According to embodiments of the present disclosure the device comprises six longitudinal struts and eighteen expandable struts.

According to another aspect of the present disclosure there is provided a method of securing a graft to a tissue comprising providing a tissue anchoring device having a plurality of longitudinal struts, wherein adjacent longitudinal struts are interconnected by a plurality of expandable struts and further wherein one of the plurality of expandable struts is angled radially outward from a remainder of the plurality of expandable struts; collapsing the tissue anchoring device within a delivery catheter; partially releasing the tissue anchoring device from the delivery catheter in a vessel such that the one of the plurality of expandable struts contacts a graft positioned within the vessel thereby stabilizing the expandable frame; and fully releasing the tissue anchoring device from the delivery catheter.

According to embodiments of the present disclosure distal expandable struts of the plurality of expandable struts each include an anchor having a tissue penetrating portion.

According to embodiments of the present disclosure the method further comprises driving the tissue penetrating portion of the anchor through the graft and the vessel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The technology is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION

Figure 1:
FIG. 1 illustrates an exemplary tissue anchoring device constructed in accordance with the principles of the present disclosure.
Figure 1:
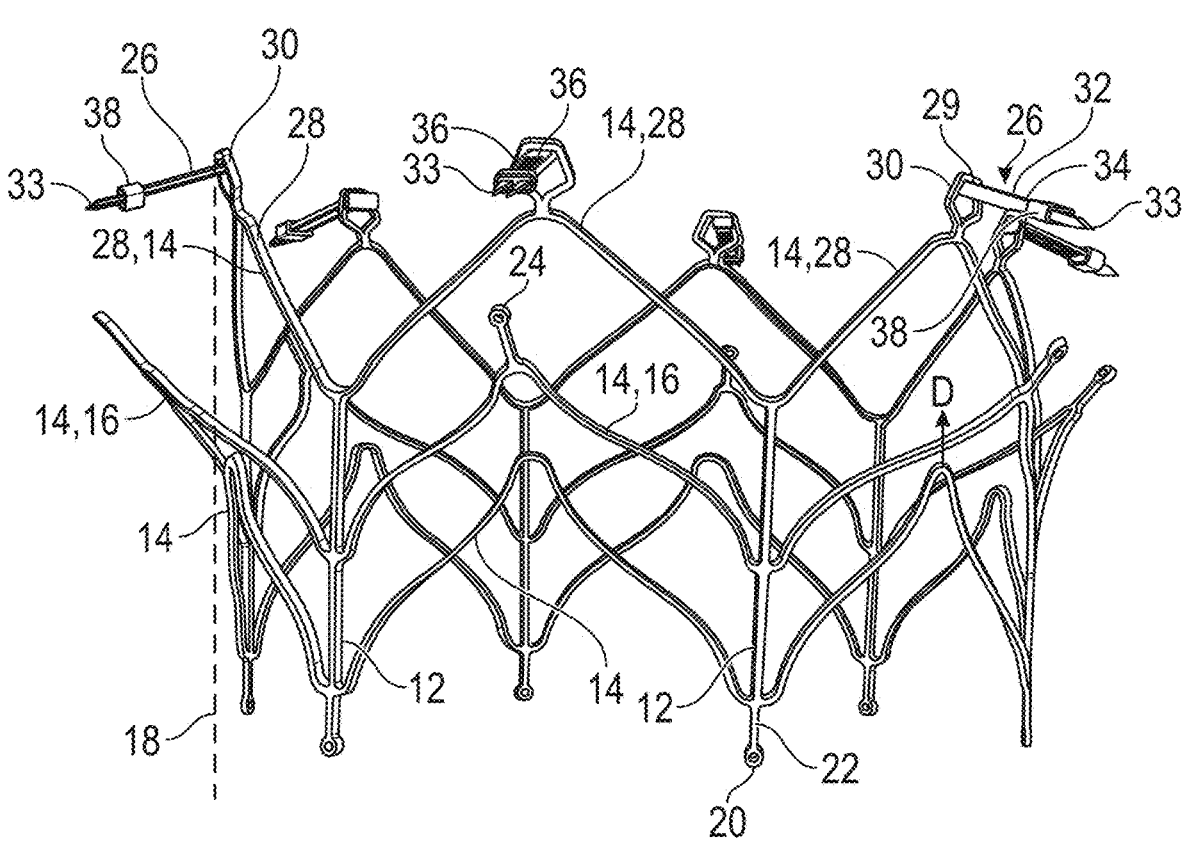

The present disclosure provides a tissue anchoring device which may be used to anchor an endoluminal device within a blood vessel. Specifically, the tissue anchoring device may be used to anchor a stent or a stent-graft in a vessel while maintaining accurate positioning and ensuring stable anchoring. The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Applicant has disclosed a graft securing device that includes tissue anchors attached around an expandable frame in U.S. Pat. No. 11,896,506, the entire contents of which is incorporated herein by reference. While experimenting with this device, the present inventors have realized that while the device can effectively anchor a graft in a vessel, delivery of the device can result in mispositioning due to a shift of the device in the vessel during deployment. Thus, according to one aspect of the present disclosure, there is provided a tissue anchoring device that includes a strut or struts that angle radially outward from the surface of the device when the device is partially deployed to thereby stabilize the device during delivery. Once the device is fully deployed these struts (termed herein "anchoring struts") are forced inward (flush with the surface of the device) by the force applied thereto by the graft/tissue. The tissue anchoring device of the present disclosure may be used to anchor any endoluminal device within any biological vessel. Examples include anchoring of grafts or stent grafts within the vasculature, anchoring of valves within the cardio vasculature, blocking of arteries and veins within the vasculature, or anchoring a vasculature bypass.

The expandable frame may be self-expanding, mechanically expanded (e.g., via a balloon) or a combination of both-self-expanding to a first diameter and then mechanically expanded to a final diameter. The expandable frame may be constructed from an alloy such as Nitinol or stainless steel or from a polymer or a combination of both. The expandable frame may be configured from longitudinal struts and rings/expandable struts and may include any number of each as long as at least one strut provides the aforementioned anchoring function. For example, the expandable frame may be constructed from an open or closed cell layout of struts, torturous (wavy) struts, or zig-zagging struts that run the length of the expandable frame from a proximal end to a distal end. The peaks or valleys of such struts may be interconnected or not. In another example, the expandable frame may be constructed from torturous rings interconnected by short linear or torturous struts.

Another example of the present tissue anchoring device may include a radially expandable frame having a plurality of longitudinal struts in which adjacent longitudinal struts are interconnected by a plurality of expandable struts. One or more of the plurality of expandable struts, e.g., a ring of expandable struts, may be angled radially outward from a remainder of the plurality of expandable struts to provide the aforementioned anchoring function during delivery. The expandable struts may be V-shaped when the device is collapsed within a delivery catheter. When released from the catheter, these struts open/expand (to form a 'dome-shape') to radially expand the device.

The expandable frame may be constructed by any one of numerous approaches known in the art, e.g., by laser cutting or etching of a tube or by laser cutting a Nitinol/stainless steel sheet and rolling and welding it to a final tube shape. Typical dimensions of the expandable frame may be, e.g., 20-40 mm in length, 25-50 mm in diameter (expanded), and 4-6.5 mm in diameter (collapsed). The struts may be 0.15-0.5 mm in width and 0.2-0.6 mm in thickness. The anchoring struts may be configured to extend 4-7 mm radially outward from a surface of the device (when the device is fully deployed on a bench, exemplified in FIG. 1).

The present tissue anchoring device may include one or more tissue anchors arranged in a specific pattern around and/or along the expandable frame (typically around a circumference close or at the distal end). The tissue anchor includes a tissue penetrating tip for penetrating graft and tissue, and anchoring thereagainst. The tissue anchors may be attached to a tab or frame that is in turn attached to a strut or ring of the expandable frame. The expandable frame and tissue anchors are fabricated such that the tissue anchors point radially outward (and optionally at a slight angle downward) from the frame regardless if the frame is expanded or collapsed. When the frame is collapsed for delivery, the tissue anchors are forced inward to a position that is roughly parallel to the longitudinal axis of the expandable frame by the delivery catheter tube. The tab or frame enable the anchor to elastically bend from a first direction in which the tissue penetrating portion points at an angle with respect to the longitudinal axis of the expandable frame (e.g., radially outward) to a second direction in which the tissue penetrating portion is generally pointing parallel to the longitudinal axis of the frame.

The present tissue anchoring device may form a part of a tissue anchoring system that also includes a delivery catheter and a deployment catheter (to deploy the tissue anchors into the tissue). The delivery catheter is used to deliver the device into a biological vessel (e.g., blood vessel), while the deployment catheter is used to drive the tissue anchors through the graft/tissue.

Referring now to FIG. 1, an exemplary tissue anchoring device is provided. FIG. 1 is an image of a prototype device representing an embodiment of tissue anchoring device 10 suitable for anchoring a graft within an artery. As shown in FIG. 1, device 10 includes an expandable frame having a plurality of longitudinal struts 12 (which may be linear or wavy/sinusoidal) interconnected by a plurality of expandable struts 14 (e.g., each pair of adjacent struts interconnected by three expandable struts 14). For example, as shown in FIG. 1, device 10 may include 6 longitudinal struts interconnected by 18 expandable struts. As will be understood by a person having ordinary skill in the art, device 10 may include more or less than 6 longitudinal struts, and accordingly, more or less than 18 expandable struts.

One expandable strut 14 of each of the three expandable struts 14 interconnecting pairs of longitudinal struts 12 (e.g., the middle strut 14) form anchoring struts 16 that angle radially outward from a surface of device 10 (shown by dotted line 18) when device 10 is fully expanded outside a vessel. When fully expanded inside a vessel (FIG. 2E), these anchoring struts 16 bend inward (e.g., by the force of device 10 expansion and counterforce of the vessel wall) and are flush with surface 18. Anchoring struts 16 may be the same length (base to peak) as other struts 14 or they may be longer so as to increase the diameter of device 10 when partially deployed.

Referring again to FIG. 1, struts 14 are roughly dome-shaped when device 10 is fully expanded. When device 10 is collapsed within a delivery catheter (FIG. 2A), struts 14 elastically bend into a V-shape, thereby reducing the distance between adjacent longitudinal struts 12 and facilitating radial collapse of device 10. Device 10 of FIG. 1 may be 25-55 mm in diameter (tip of eyelet on zig 16) when expanded and 4-6.5 mm in diameter when collapsed. When collapsed, the distance between adjacent struts 12 may be 2-3.4 mm, and when expanded that distance may be 12-20 mm. Longitudinal struts 12 may be 5-25 mm in length. Struts 12 and 14 may have a square or round profile with a width/diameter of 0.15-0.5 mm. The force exerted by device 10 expanded in a vessel of 19-36 mm diameter may be 8-16 Newtons. The force required to bend struts 16 flush with a surface 18 of device 10 may be 4-6 Newtons.

Device 10 may include eyelets 20 attached to a proximal end 22 of each strut 12. Eyelets 20 may be used to retrieve the device once partially or completely deployed within the vessel. Eyelets 20 may be engaged by recesses 21 in holder 23 that is a part of delivery catheter 50 (FIG. 2D). Outer sheath 51 may cover recesses 21 and eyelets 20 (engaged therein), thus preventing release of device 10 from the delivery catheter. A partially deployed device 10 may be re-sheathed and recovered if need be as long as recesses 21 are covered by sheath 51. Referring again to FIG. 1, additional eyelets 24 positioned at the peak of struts 16 may be used for markers (radiopaque) or to lengthen anchoring strut 16 so as to increase the diameter of device 10 when partially deployed (and better anchor against the graft into which it is deployed). Accordingly, eyelets 24 may serve as the initial contact point between device 10 and the graft wall during deployment of device 10.

Device 10 may include one or more tissue anchors 26 arranged in a specific pattern around and/or along the expandable frame. As shown in FIG. 1, anchors 26 are attached to distal longitudinal struts 28 through support frame 30. Each tissue anchor 26 includes base 29 attached to support frame 30 (that enables anchor 26 to transition from a collapsed configuration to a deployed configuration) and anchor body 32 that includes tissue penetrating portion 34 having at least two prongs 36 (each having a sharp tip 33) that are restrained for delivery in a co-linear configuration (juxtaposed along their length) by a restraining element, e.g., sleeve/collar 38, capable of sliding along anchor body 32. When sleeve/collar 38 is pushed backward towards the expandable frame, prongs 36 are released and splay out to a tissue anchoring configuration. Accordingly, when tissue penetrating portion 34 penetrates the graft/tissue (e.g., when tissue penetrating portion 34 moves relative to the graft/tissue), the graft/tissue pushes against sleeve/collar 38 and maintains the position of sleeve/collar 38 relative to the graft/tissue as tissue penetrating portion 34 penetrates the graft/tissue. As sleeve/collar 38 is pushed back (by the graft/tissue), sleeve/collar 38 moves proximally relative to prongs 36 as tissue penetrating portion 34 penetrates the graft/tissue to thereby release prongs 36, and prongs 36 splay out (deflect away from each other) to anchor against the far side of the graft and/or tissue.

Figure 2A:
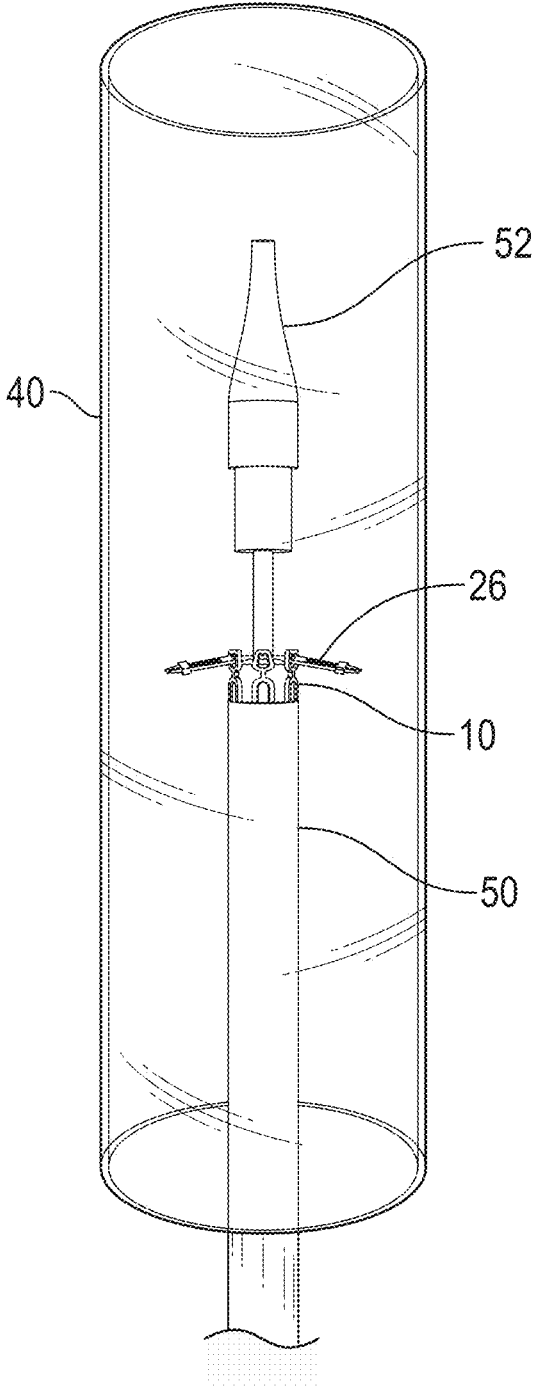
FIG. 2A to 2G illustrate delivery of the device of FIG. 1 into a clear tube representing a vessel.
Figure 2B:
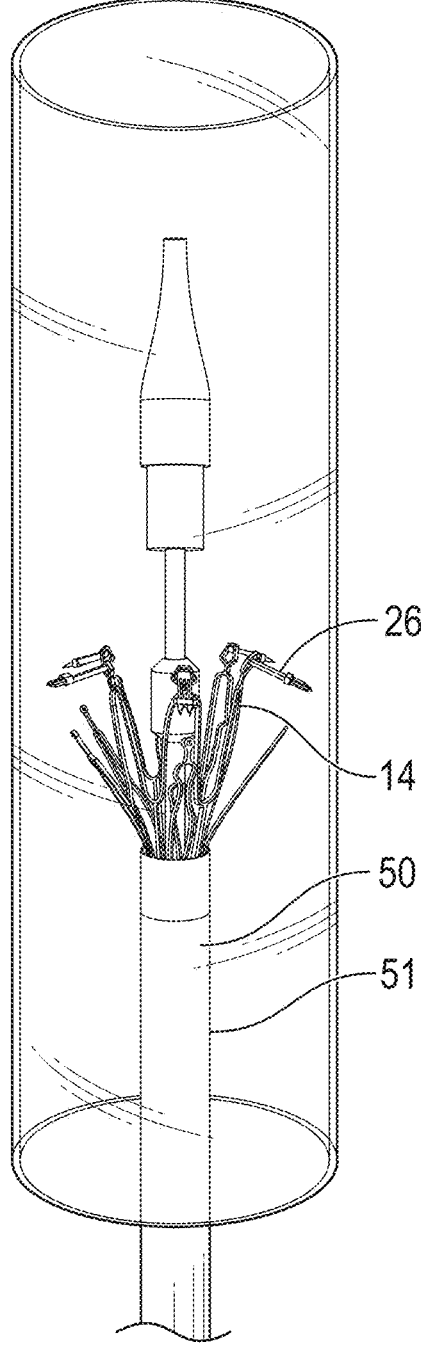
Figure 2C:
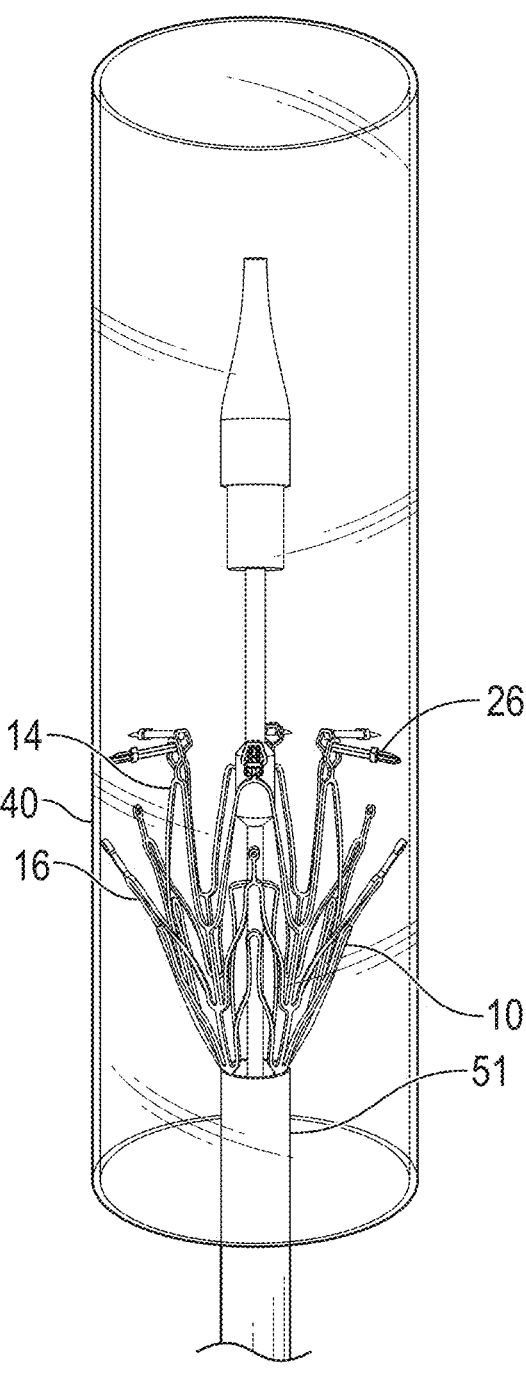
Figure 2D:
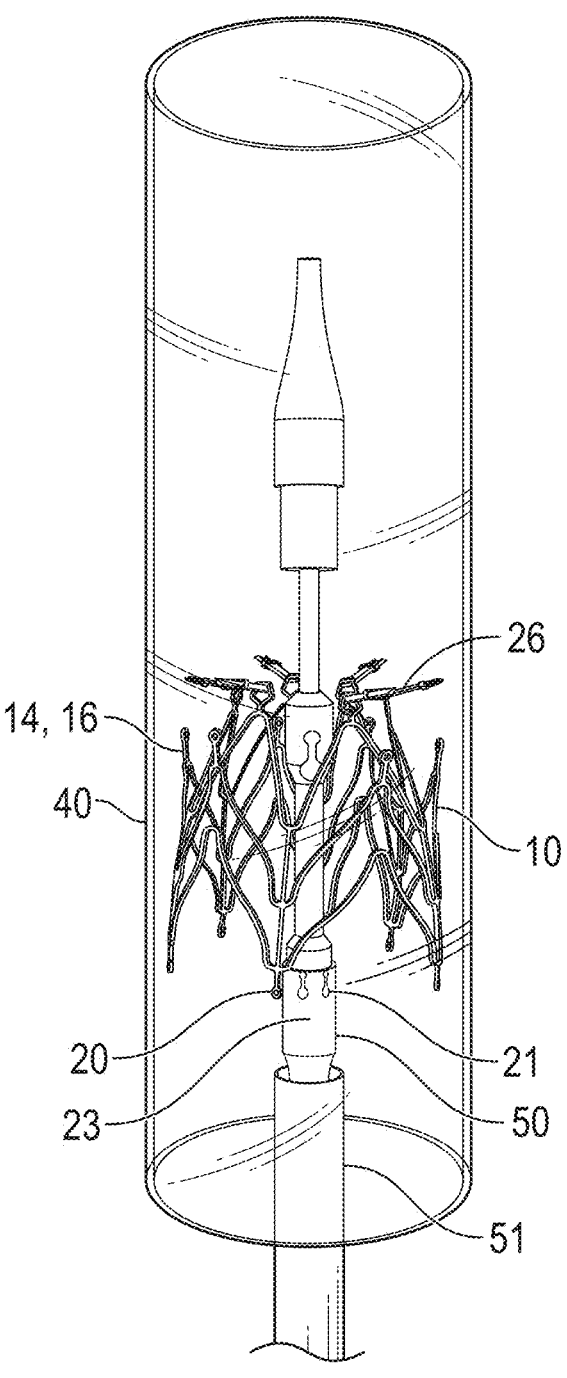
Figure 2E:
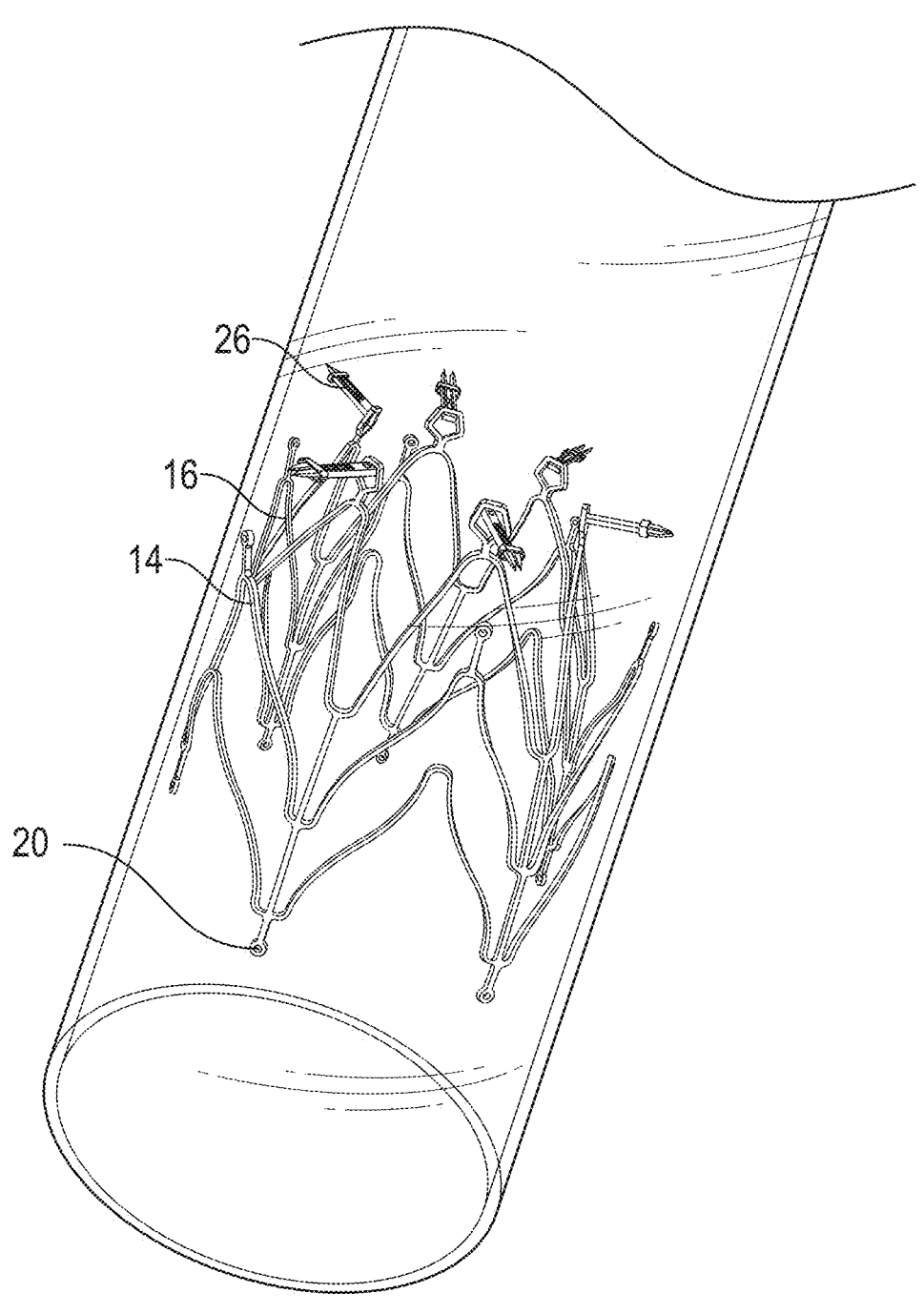

Referring now to FIGS. 2A to 2G, delivery of device 10 is provided. As shown in FIG. 2A, delivery catheter 50 having nose cone 52 maintains device 10 in a collapsed configuration in a 'vessel' 40. As nose cone 52 moves forward, anchors 26 are released outward to the anchoring positions shown in FIG. 2A. As shown in FIG. 2B, as sheath 51 is pulled back (proximally), distal struts 14 emerge and begin to expand outward. When struts 16 emerge and expand, they angle outward away from a longitudinal plane of distal struts 14, as shown in FIG. 2C. As shown in FIG. 2D, struts 16 may contact the inner wall of vessel 40 and stabilize device 10 until full deployment of device 10 (e.g., release of eyelets 20 from recesses 21 when sheath 51 is pulled back to uncover recesses 21), as shown in FIG. 2E. Once device 10 is fully deployed and struts 16 are forced flush with the surface of device 10 (e.g., struts 14 and 16 are in the same radial plane), as shown in FIG. 2E, delivery catheter 50 may be removed and anchors 26 may then be driven through the graft and/or the vessel wall using a dedicated balloon catheter, e.g., deployment dual balloon catheter 60.

Figure 2F:
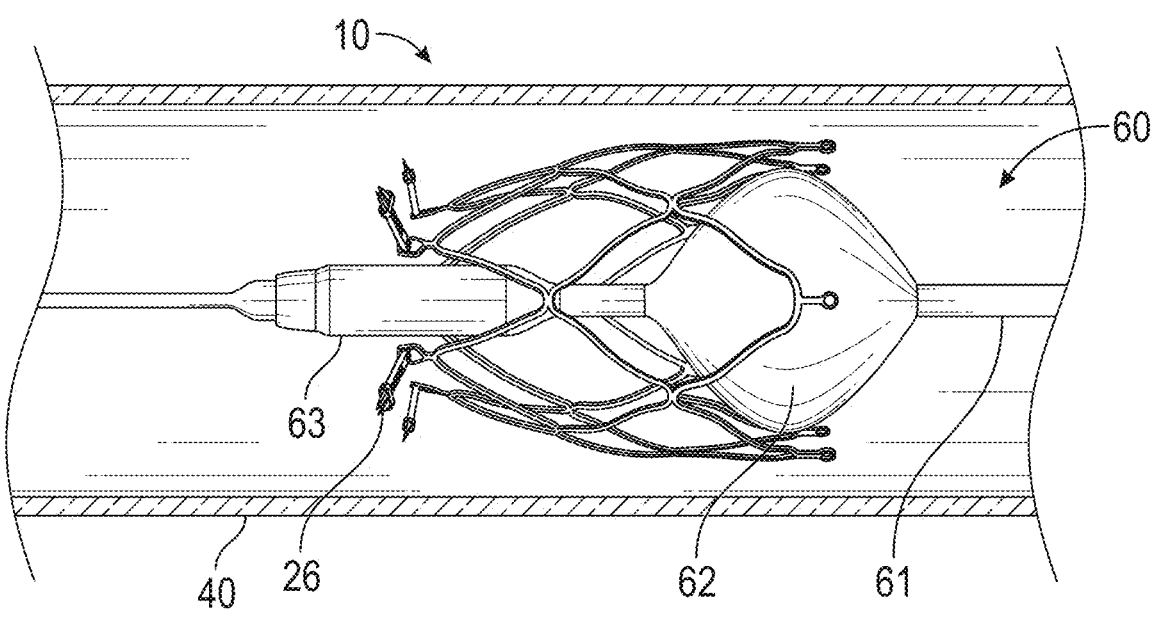

As shown in FIG. 2F, balloon catheter 60 may include multi-lumen elongated shaft 61, proximal locking balloon 62 disposed on a distal region of elongated shaft 61, and distal activation balloon 63 disposed on elongated shaft 61 distal to locking balloon 62. Locking balloon 62 may be a low-pressure compliant balloon, and may be inflated to center balloon catheter 60 within the endovascular graft while securing device 10 to prevent any axial movement of device 10 during activation of activation balloon 63. Activation balloon 63 may be a semi-compliant balloon, and may be inflated to apply a radial force to expand the distal region of device 10 and cause anchors 26 to penetrate the graft/tissue. The outer diameter (e.g., free flow diameter) of activation balloon 63 may be about 1 mm larger than the inner diameter of the largest stent graft device 10 is indicated for. Each of locking balloon 62 and activation balloon 63 may have a separate inflation port to allow for independent inflations thereof. Inflation of locking balloon 62 and activation balloon 63 may be monitored via fluoroscopy.

Table 1 copied below summarizes the diameter of activation balloon 63 when pressurized on the bench in an unconstrained configuration (e.g., not within a stent graft and vessel).

TABLE 1

| Recommended Pressure/Volume | Balloon Unconstrained Diameter [mm] |
|---|---|
| 7 ml | 20 |
| 1.0 atm | 21 |
| 1.5 atm | 22 |
| 2.0 atm | 23 |
| 2.5 atm | 24 |
| 3.0 atm | 25 |
| 3.5 atm | 26 |
| 4.0 atm | RBP |

Although the free, unconstrained diameter of activation balloon 63 is preferably larger than the target vessel diameter, minimal contact pressure is transferred to the stent graft or vessel wall during staple activation due to the construction and behavior of the semi-compliant balloon.

Figure 2G:
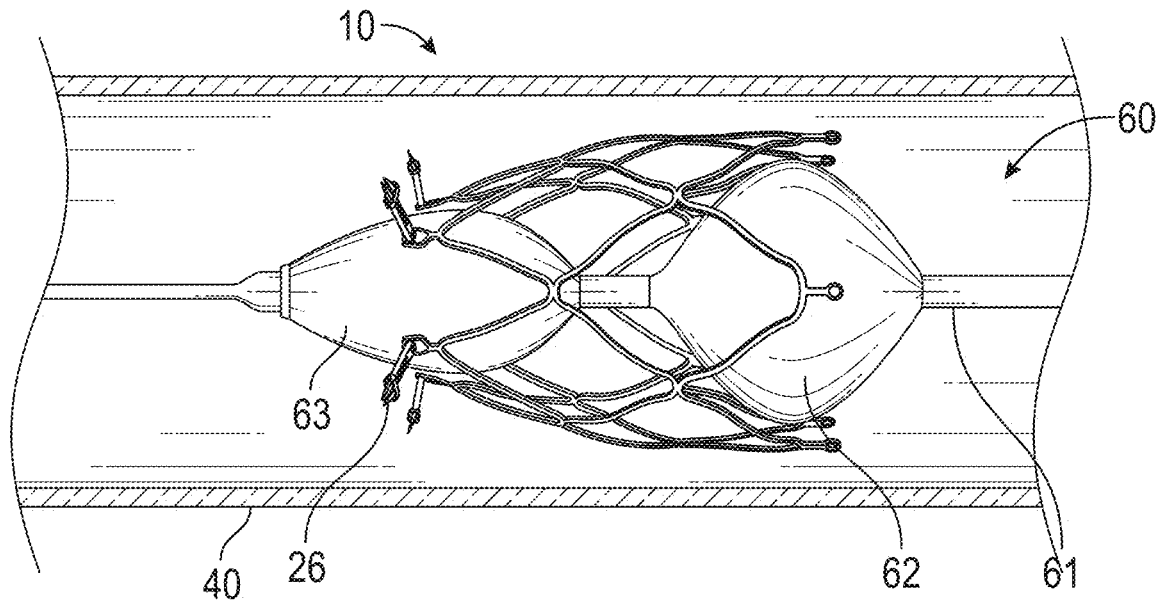

Activation balloon 63 may be spaced apart from locking balloon 62 by a distance such that, upon inflation of locking balloon 62 within vessel 40, which pins at least the proximal region of the expandable frame of device 10 between the inner wall of vessel 40 and locking balloon 62 to thereby prevent axial movement of device 10 within vessel 40, as shown in FIG. 2F, activation balloon 63 may be inflated to supply the force required to radially expand at least the distal region of the expandable frame of device 10 and cause anchors 26 to penetrate the graft/tissue, as shown in FIG. 2G, such that device 10 is in a fully implanted configuration within vessel 40. In the fully implanted configuration, the expandable frame may conform to the graft/vessel (e.g., have a cylindrical shape along its length) with anchors 26 deployed through the graft/tissue.

As is mentioned herein, device 10 may be configured for aortic aneurysm repair. Such repair may be carried out as follows. A delivery catheter having device 10 collapsed therein is advanced over a wire through the vasculature from an access site (e.g., femoral) to a deployment target (e.g., abdominal aneurysm) where a graft has been previously deployed and positioned. Device 10 may be partially unsheathed by delivery catheter 50 to partially deploy the expandable frame and release the anchoring struts. Once device 10 is stabilized by the anchoring struts, e.g., struts 16, device 10 may be fully deployed by retracting sheath 51 to expose recesses 21, and delivery catheter 50 may be removed. A dual balloon catheter, e.g., balloon catheter 60, may then be advanced over the wire, such that the balloons, e.g., locking balloon 62 and activation balloon 63, are positioned within device 10 in their collapsed delivery states. Radiopaque markers on the balloon catheter shaft, e.g., elongated shaft 61, enable accurate positioning of the balloons. For example, the proximal balloon, e.g., locking balloon 62, may be positioned by aligning its marker with the rear end of device 10. Locking balloon 62 (nylon, Pebax, Polyurethane, length 10-15 mm) may then be inflated to about 0.5-1 atm and a diameter of about 25-40 mm to lock the proximal end of device 10 against the graft or tissue while radially centering the distal balloon, e.g., activation balloon 63, at the site of the anchors, e.g., anchors 26. Activation balloon 63 (nylon, Pbax, Polyurethane, length 15-35 mm) may then be inflated to about 1-4 atm and a diameter of about 20-35 mm to force anchors 26 through the graft and aortic wall and effectively staple the graft to the tissue. As used herein the term "about" refers to ±10%.

Figure 3:
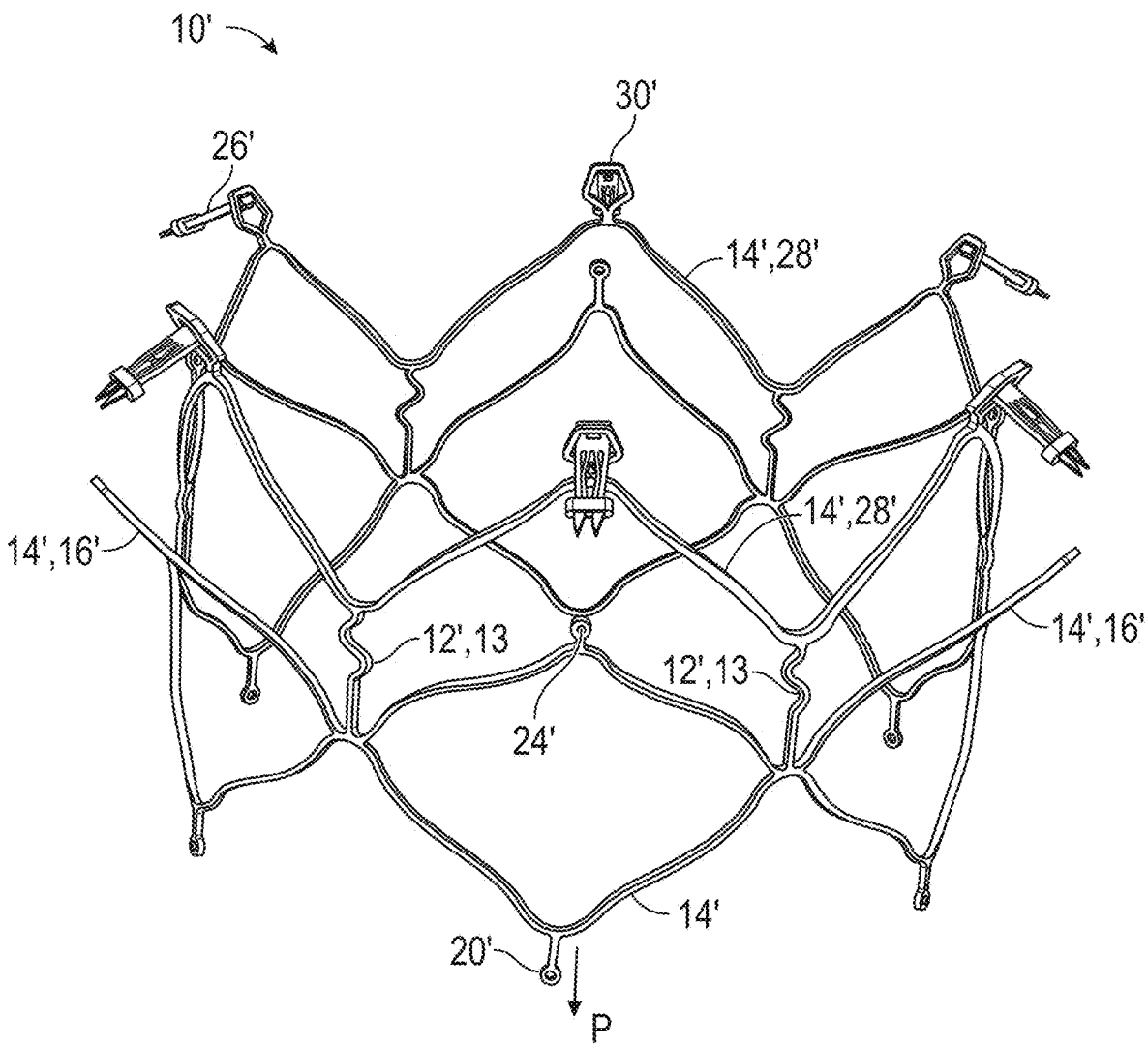
FIG. 3 illustrates an alternative exemplary tissue anchoring device constructed in accordance with the principles of the present disclosure.

Referring now to FIG. 3, another exemplary tissue anchoring device is provided. Tissue anchoring device 10' may be constructed similar to tissue anchoring device 10, with corresponding components denoted by like-prime reference numerals. For example, proximal struts 14' having eyelets 20', struts 14', 16' having eyelets 24' and struts 14', 28' having support frame 30' coupled to anchors 26' correspond to proximal struts 14 having eyelets 20, struts 14, 16 having eyelets 24 and struts 14, 28 having support frame 30 coupled to anchors 26. Device 10' differs from device 10 in that at least a portion 13 of longitudinal struts 12' (that are shorter in this configuration) has a wavy or sinusoidal shape (e.g., S-shaped). Accordingly, device 10' may have an overall length that is shorter than device 10. Portion 13 serves as a 'spring' to dampen longitudinal forces on device 10' when deployed within a graft or vessel and when anchors 26' of device 10' are forced into the graft and tissue, e.g., using a balloon catheter.

In addition, as shown in FIG. 3, proximal expandable struts 14' of device 10' may point in a proximal direction P (opposite to the rest of struts 14') as opposed to the embodiment of device 10 of FIG. 1 where the same proximal expandable struts 14 point distally D (in the same direction as the other struts 14). The proximally-pointing struts 14' enhance traction between the locking balloon used to stabilize device 10' against the graft when anchors 26' are forced into the graft and tissue. Moreover, eyelets 20' may have an increased neck length to provide more flexibility and improve control of device 10' during release of eyelets 20' from recesses 21 of the delivery catheter, as well as during repositioning of device 10, if necessary. As will be understood by a person having ordinary skill in the art, device 10' may be delivered and deployed using the delivery and deployment catheters described herein, e.g., delivery catheter 50 and balloon catheter 60, in the same manner as device 10. Alternatively, any of the tissue anchoring devices described herein, e.g., device 10 and device 10', may be deployed using balloon catheter 60' having activation balloon 62', as described in further detail below with regard to FIGS. 6A to 6E.

Figures 4A, 4B, 4C:
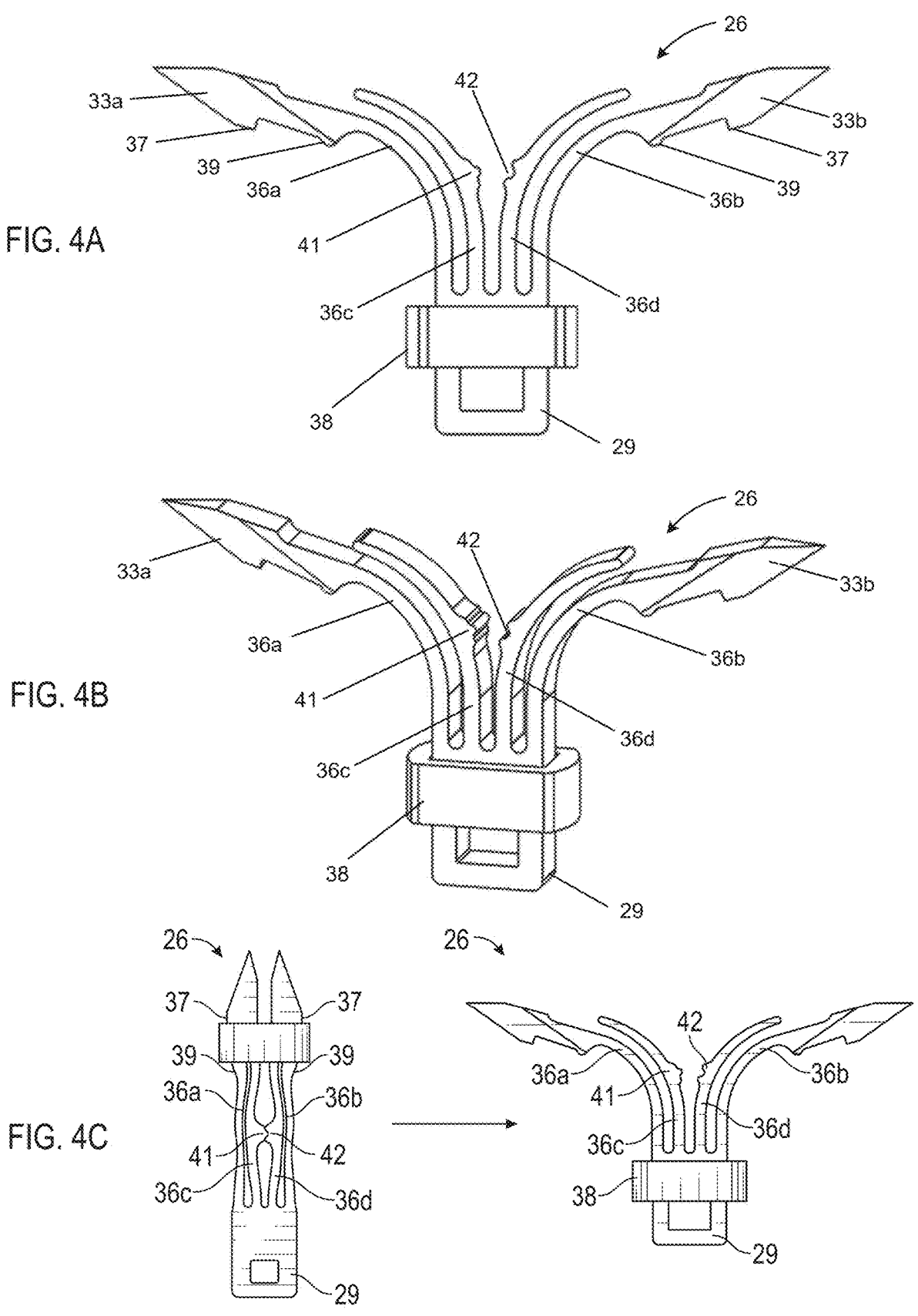
FIGS. 4A to 4C illustrate an exemplary anchor of the tissue anchoring device having an exemplary anti-buckling mechanism constructed in accordance with the principles of the present disclosure.

Referring now to FIGS. 4A to 4C, an exemplary anchor of the tissue anchoring devices described herein, is provided. As shown in FIGS. 4A to 4C, anchor 26 may comprises four prongs, e.g., external prongs 36a, 36b and internal prongs 36c, 36d (collectively referred to herein as prongs 36). Prongs 36 are resilient and may be made of a shape memory material, e.g., Nitinol. For example, prongs 36 may be pre-shaped to assume a pre-shaped unrestrained configuration in which prongs 36 are deflected away from each other in an open unrestrained state. Each of external prongs 36a, 36b may include a respective penetration tip 33a, 33b (collectively referred to herein as penetration tips 33), and may be positioned next to an internal prong, e.g., internal prongs 36c, 36d, respectively, so as to form two pairs of prongs 36a/36c and 36b/36d. Accordingly, the two pairs of prongs 36a/36c and 36b/36d may be configured to deflect away from each other when assuming an unrestrained, deployed state. In some embodiments, internal prongs 36c, 36d may be slidable along the adjacent external prongs 36a, 36b, respectively, when deflecting outwards towards the unrestrained state. Moreover, internal prongs 36c, 36d may apply a deflecting force on the adjacent external prongs 36a, 36b, respectively, when deflecting towards the unrestrained state.

As shown in FIGS. 4A to 4C, anchor 26 further includes restraining sleeve/collar 38 disposed over and slidable along prongs 36. The length of sleeve 38 may be shorter than the length of prongs 36, such that sleeve 38 is slidable over and along the prongs 36 between the penetration tips 33 and base 29. As shown in FIG. 4C, sleeve 38 may be moved between a first distal position, e.g., adjacent to tips 33, where prongs 36 are in a restrained state (left figure), and a second proximal position, e.g., adjacent base 29, thereby releasing prongs 36 and permitting prongs 36 to deflect away from each other in the unrestrained state (right figure). As described above, as anchor 26 penetrates the graft/tissue, the counterforce applied to sleeve 38 by the graft/tissue causes sleeve 38 to move from the first distal position to the second proximal position, to thereby deploy prongs 36 to their unrestrained state.

In some embodiments, base 29 of anchor 36 may be wider than the internal cross section of sleeve 38, such that sleeve 38 is prevented from sliding proximally over base 29 of anchor 26. Moreover, anchor 26 may include one or more distal stops 37 disposed adjacent to penetration tips 33, and configured to block sleeve 38 from sliding distally relative to prongs 36 and over the distal end of anchor 26, as shown in FIG. 4C, and accordingly, block prongs 36 from moving proximally relative to sleeve 38 and slipping out of sleeve 38. For example, distal stops 37 may be formed as part of penetration tips 33 and/or may be shaped as a rib protruding laterally outwards from external prongs 36a, 36b and extending beyond an internal cross section of sleeve 38.

In addition, anchor 26 may include one or more proximal stops 39 disposed proximal to distal stops 37 (e.g., by a distance that is at least the length of sleeve 38), and configured to temporarily block sleeve 38 from sliding proximally relative to prongs 36, as shown in FIG. 4C. For example, proximal stops 39 may be shaped as a rib protruding laterally outwards from external prongs 36a, 36b and extending beyond an internal cross section of sleeve 38. As prongs 36 are resilient, upon application of at least a predetermined amount of force to proximal stops 39 by sleeve 38, prongs 36 may deflect inward towards each other as sleeve 38 moves proximally relative to proximal stops 39 to thereby permit sleeve 38 to move from the first distal position towards the second proximal position, as shown in FIG. 4C.

In the restrained state, prongs 36 are juxtaposed throughout their length. Thus, as prongs 36 transition from the restrained state towards the unrestrained state during deployment and penetration into the graft/tissue, forces applied to the proximal portion of prongs 36 (e.g., "on axis" forces) while penetration tips 33 are held by the graft/tissue may cause anchor 26 to buckle. Buckling causes movement between juxtaposed prongs, e.g., internal prongs 36c, 36d, (e.g., due to relative axial movement of each prong relative to the juxtaposed prong), expressed as longitudinal movement between adjacent prongs. Accordingly, anchor 26 may include an anti-buckling mechanism, e.g., a buckling prevention lock, configured to provide friction to stop relative movement between the juxtaposed prongs, e.g., internal prongs 36c, 36d, and prevent buckling of anchor 26.

For example, as shown in FIGS. 4A and 4B, the anti-buckling mechanism may be formed by protrusion 41 (e.g., a curved bump) protruding inwardly from a first internal prong, e.g., internal prong 36c, towards a juxtaposed second internal prong, e.g., internal prong 36d, and recess 42 formed in internal prong 36*d* and facing protrusion 41, such that in a juxtaposed configuration of internal prongs 36*c*, 36*d* (e.g., in the restrained state), protrusion 41 is accommodated by recess 42, as shown in FIG. 4C, to thereby form the buckling prevention lock. In some embodiments, protrusion 41 may be tongue-shaped. As shown in FIGS. 4A to 4C, the buckling prevention lock may be disposed within a middle region of anchor 26.

As anchor 26 penetrates the graft/tissue, the juxtaposed prongs will effectively behave as a single prong, e.g., doubling the force without having a single prong, to thereby reduce/eliminate the risk of plastic deformation of anchor 26. As sleeve 38 is moved proximally towards base 29 and away from the buckling prevention lock, protrusion 41 will disengage from recess 42 to permit prongs 36*a*, 36*c* and prongs 36*b*, 36*d* to deflect away from each other towards the unrestrained state, as shown in FIG. 4C. As will be understood by a person having ordinary skill in the art, protrusion 41 may be formed on internal prong 36*d* and recess 42 may be formed in internal prong 36*c*. Moreover, the internal prongs may include more than one set of protrusion/recess, and the buckling prevention lock(s) further may be disposed at positions along the internal prongs other than that shown in FIGS. 4A to 4C. Any of the anchoring tissue devices described herein, e.g., devices 10, 10', may include the anchor embodiment of FIGS. 4A to 4C.

Figures 5A, 5B, 5C:
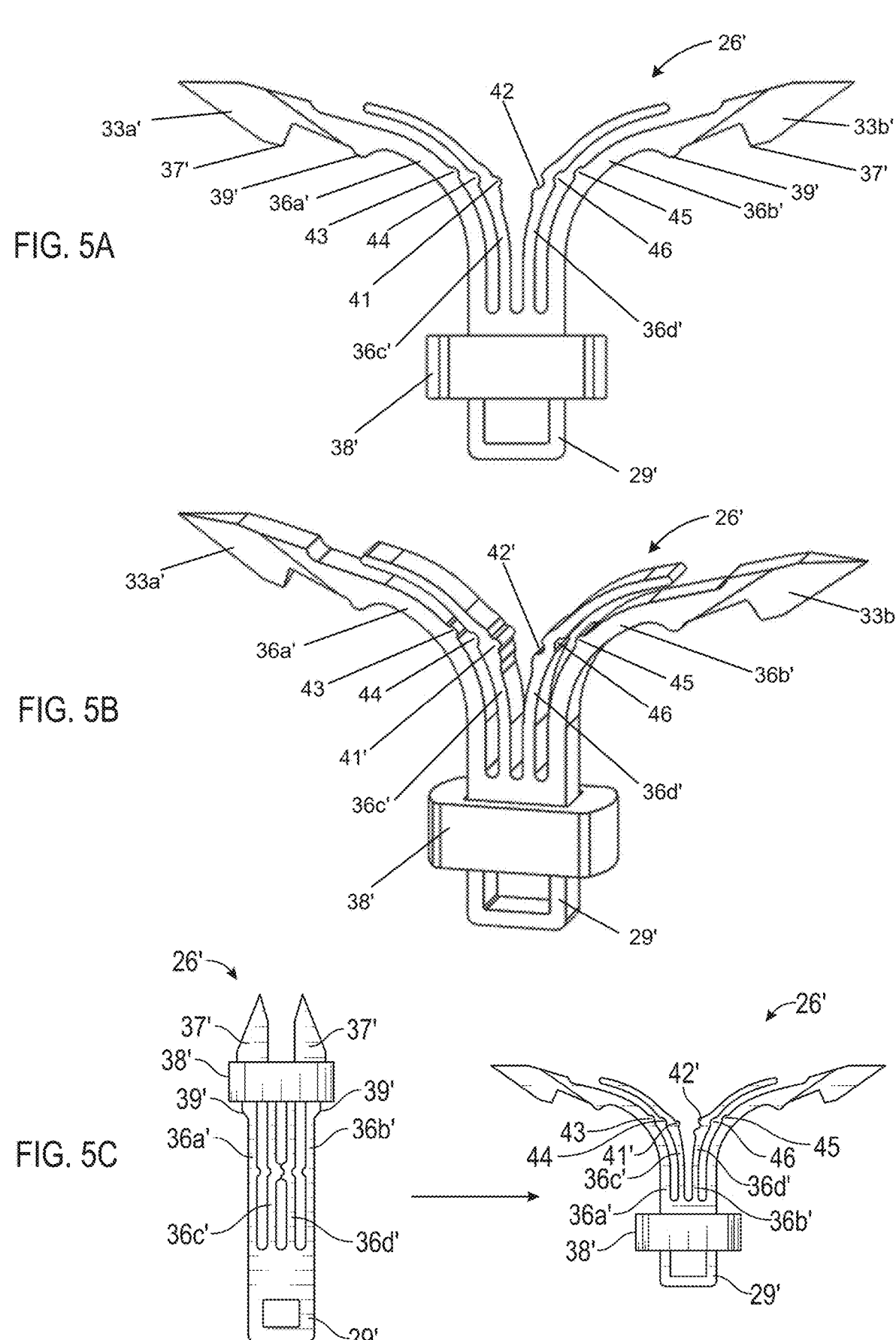
FIGS. 5A to 5C illustrate another exemplary anchor of the tissue anchoring device having an alternative exemplary anti-buckling mechanism constructed in accordance with the principles of the present disclosure.

Referring now to FIGS. 5A to 5C, an alternative exemplary anchor of the tissue anchoring devices described herein, is provided. Anchor 26' may be constructed similar to anchor 26. For example, base 29' of anchor 26', slidable restraining sleeve 38', external prongs 36*a*', 36*b*' having distal stops 37', proximal stops 39', and penetration tips 33*a*', 33*b*', respectively, and internal prongs 36*c*', 36*d*' having protrusion 41' and recess 42', respectively, correspond with base 29 of anchor 26, slidable restraining sleeve 38, external prongs 36*a*, 36*b* having distal stops 37, proximal stops 39, and penetration tips 33*a*, 33*b*, respectively, and internal prongs 36*c*, 36*d* having protrusion 41 and recess 42, respectively. Anchor 26' differs from anchor 26 in that anchor 26' may further include one or more additional buckling prevention locks formed between juxtaposed prongs.

For example, as shown in FIGS. 5A and 5B, a second buckling prevention lock may be formed by protrusion 43 (e.g., a curved bump) protruding inwardly from a first external prong, e.g., external prong 36*a*', towards a juxtaposed first internal prong, e.g., internal prong 36*c*', and recess 44 formed in internal prong 36*c*' and facing protrusion 43, such that in a juxtaposed configuration of prongs 36*a*', 36*c*' (e.g., in the restrained state), protrusion 43 is accommodated by recess 44, as shown in FIG. 5C, to thereby form the buckling prevention lock. Additionally or alternatively, a third buckling prevention lock may be formed by protrusion 45 (e.g., a curved bump) protruding inwardly from a second external prong, e.g., external prong 36*b*', towards a juxtaposed second internal prong, e.g., internal prong 36*d*', and recess 46 formed in internal prong 36*d*' and facing protrusion 45, such that in a juxtaposed configuration of prongs 36*b*', 36*d*' (e.g., in the restrained state), protrusion 45 is accommodated by recess 46, as shown in FIG. 5C, to thereby form the buckling prevention lock. In some embodiments, protrusions 43, 45 may be tongue-shaped. As shown in FIGS. 5A to 5C, the buckling prevention locks may be disposed within a middle region of anchor 26'. In some embodiments, the buckling prevention locks may be staggered along the length of anchor 26', e.g., the buckling prevention lock formed by juxtaposed prongs 36*c*', 36*d*' may be disposed distal or proximal to the buckling prevention lock formed by juxtaposed prongs 36*a*', 36*c*' and/or the buckling prevention lock formed by juxtaposed prongs 36*b*', 36*d*'.

As anchor 26' penetrates the graft/tissue, the juxtaposed prongs will effectively behave as a single prong, e.g., doubling the force without having a single prong, to thereby reduce/eliminate the risk of plastic deformation of anchor 26'. As sleeve 38' is moved proximally towards base 29' and away from the buckling prevention locks, protrusions 41', 43, 45 will disengage from recesses 42', 44, 46, respectively, to permit prongs 36*a*', 36*c*' and prongs 36*b*', 36*d*' to deflect away from each other towards the unrestrained state, as shown in FIG. 5C. As will be understood by a person having ordinary skill in the art, protrusion 41' may be formed on internal prong 36*d*' and recess 42' may be formed in internal prong 36*c*', protrusion 43 may be formed on internal prong 36*c*' and recess 44 may be formed in external prong 36*a*', and/or protrusion 45 may be formed on internal prong 36*d*' and recess 46 may be formed in external prong 36*b*'. Moreover, the each pair of juxtaposed prongs may include more than one set of protrusion/recess, and the buckling prevention lock(s) further may be disposed at positions along the external/internal prongs other than that shown in FIGS. 5A to 5C. Any of the anchoring tissue devices described herein, e.g., devices 10, 10', may include the anchor embodiment of FIGS. 5A to 5C.

Figure 6A:
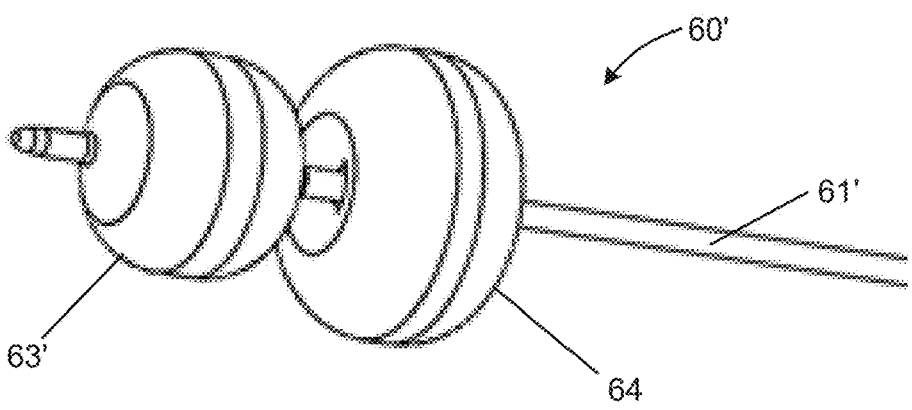
FIGS. 6A to 6C illustrate an exemplary dual balloon catheter constructed in accordance with the principles of the present disclosure.
Figure 6B:
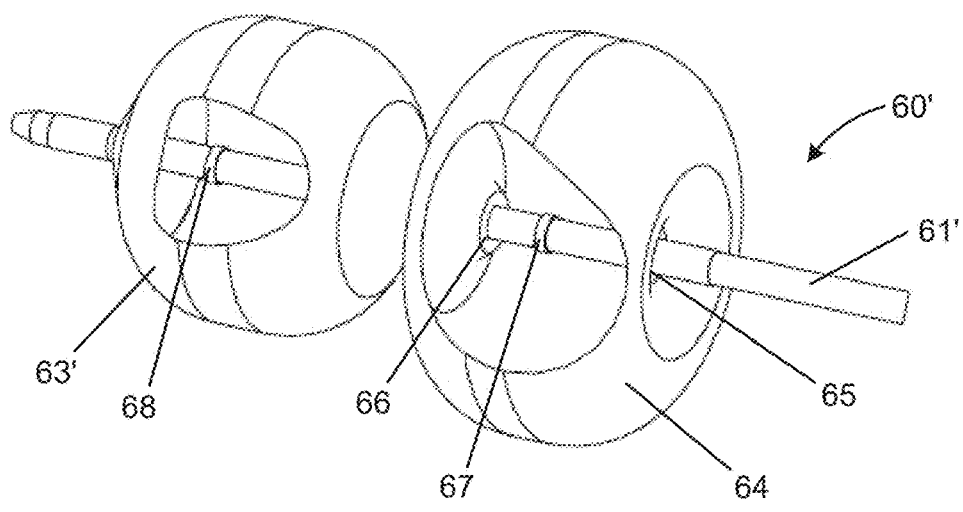
Figure 6C:
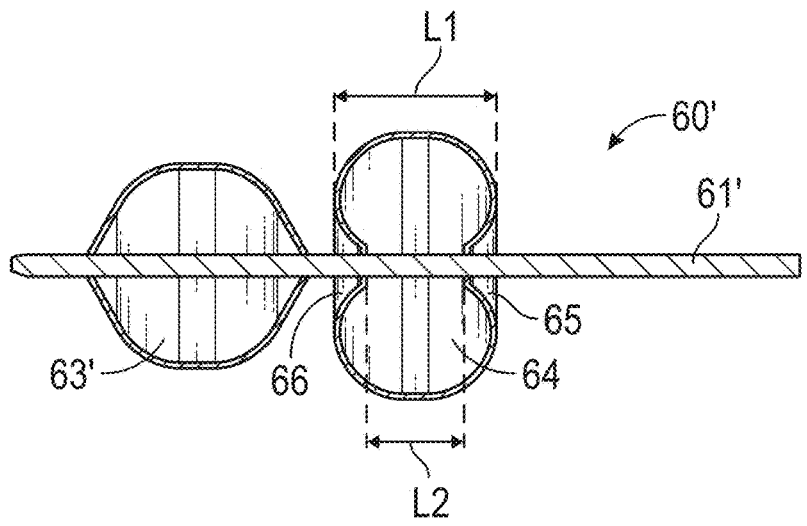

Referring now to FIGS. 6A to 6E, an alternative exemplary deployment dual-balloon catheter for deploying the tissue anchoring devices described herein, is provided. Balloon catheter 60' may be constructed similar to balloon catheter 60. For example, multi-lumen elongated shaft 61' and activation balloon 63' disposed on elongated shaft 61' distal to locking balloon 64 corresponds with multi-lumen elongated shaft 61 and activation balloon 63 disposed on elongated shaft 61 distal to locking balloon 62. Balloon catheter 60' differs from balloon catheter 60 in that locking balloon 64 may be coupled to elongated shaft 61' within itself, such that locking balloon 64 comprises a toroidal-like shape (e.g., donut-like shape) in its inflated state. For example, as shown in FIG. 6C, locking balloon 64 may be coupled to elongated shaft 61', e.g., at proximal connection 65 and distal connection 66, in a manner such that the distance between proximal connection 65 and distal connection 66 (e.g., length L2) may be shorter than the length between the widest ends of locking balloon 64 when locking balloon 64 is in its inflated state (e.g., length L1). Thus, in the inflated state, the proximal and distal ends of locking balloon 64 will extend proximal and distally, respectively, beyond proximal connection 65 and distal connection 66, respectively.

Accordingly, the distance between the centers of locking balloon 64 and activation balloon 63' may be less than the distance between the centers of locking balloon 62 and activation balloon 63 (e.g., by about 1.5-3 mm), to thereby accommodate shorter tissue anchoring devices. Moreover, as shown in FIG. 6B, balloon catheter 60 may have two radiopaque marker bands, e.g., marker 68 located in the middle of the shaft activation balloon 63, and marker 67 located on the cone end of locking balloon 62, to allow accurate positioning of balloon catheter 60 relative to the device 10 prior to inflation. As will be understood by a person having ordinary skill in the art, in some embodiments, proximal connection 65 may be disposed more proximally relative to elongated shaft 61', such that, in the inflated state, proximal connection 65 is the proximal-most end of locking balloon 64 (like the proximal portion of locking balloon 62).

Figure 6D:
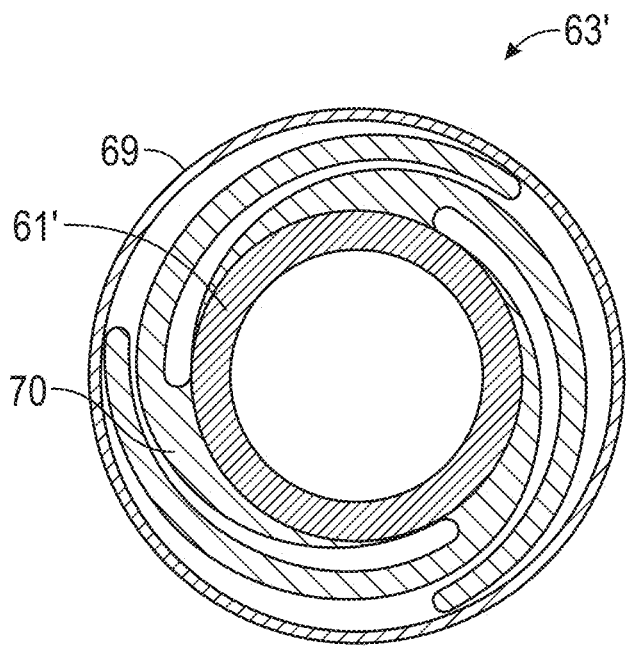
FIG. 6D is a cross-sectional view of the activation balloon of the dual balloon catheter of FIG. 6A in a collapsed delivery state.
Figure 6E:
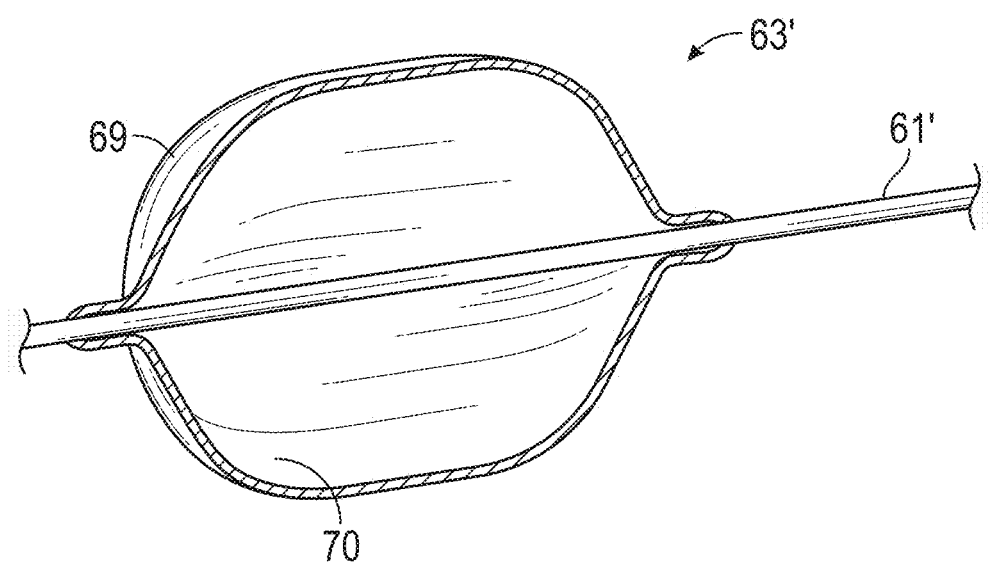
FIG. 6E is a cross-sectional view of the activation balloon in an expanded state.

As shown in FIGS. 6D and 6E, the activation balloon of the balloon catheter, e.g., activation balloon 63', may be formed of two separate layers, e.g., expandable outer sleeve 69 and foldable internal balloon 70 disposed within an interior of outer sleeve 69. Internal balloon 70 may be formed of, e.g., Pebax, and functions as a conventional foldable compliant balloon. Flexible outer sleeve 69 acts as a protection layer that prevents puncturing of internal balloon 70 while enabling a smooth and round interface with the tissue anchor device during the inflation and unfolding of internal balloon 70 from a collapsed delivery state, as shown in FIG. 6D, to an expanded state, as shown in FIG. 6E.

It is the intent of the applicant(s) that all publications, patents, and patent applications referred to in this specification are to be incorporated in their entirety by reference into the specification, as if each individual publication, patent, or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

While various illustrative embodiments of the invention are described above, it will be apparent to one skilled in the art that various changes and modifications may be made therein without departing from the invention. For example, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. The appended claims are intended to cover all such changes and modifications that fall within the true scope of the invention.

What is claimed:

1. A tissue anchoring device for securement within a blood vessel, the tissue anchoring device comprising:
   a radially expandable frame configured to transition between a collapsed configuration and an expanded configuration, the frame comprising a distal portion, a proximal portion, and a plurality of longitudinal struts interconnected by a plurality of expandable struts,
   wherein, in the expanded configuration, a ring of expandable struts of the plurality of expandable struts is angled radially outward relative to a remainder of the plurality of expandable struts, the distal portion and the ring of expandable struts configured to transition to the expanded configuration such that the ring of expandable struts is sized and shaped to contact an inner wall within the blood vessel to stabilize the frame for full deployment when the proximal portion transitions from the collapsed configuration to the expanded configuration,
   wherein peaks of the ring of expandable struts are configured to face in a distal direction and peaks of the proximal-most expandable struts at a proximal end of the tissue anchoring device of the plurality of expandable struts are configured to face in a proximal direction such that a distance between the peaks of the ring and the peaks of the proximal-most expandable struts decreases when the frame is expanded, wherein the peaks of the ring of expandable struts are longitudinally aligned with the peaks of the proximal-most expandable struts, and
   wherein, in the expanded configuration, the proximal-most expandable struts and the distal-most expandable struts at a distal end of the tissue anchoring device of the plurality of expandable struts are in the same radial plane.

2. The device of claim 1, wherein each of the plurality of expandable struts interconnecting adjacent longitudinal struts is configured to expand circumferentially from a V shape in the collapsed configuration to a dome shape in the expanded configuration.

3. The device of claim 1, wherein one or more peaks of the ring of expandable struts comprises an eyelet.

4. The device of claim 1, wherein the ring of expandable struts of the plurality of expandable struts is configured to contact the inner wall prior to the remainder of the plurality of expandable struts as the frame transitions from the collapsed configuration to the expanded configuration within the blood vessel.

5. The device of claim 1, wherein at least a portion of at least one longitudinal strut of the plurality of longitudinal struts comprises an S shape.

6. The device of claim 5, wherein the at least one longitudinal strut of the plurality of longitudinal struts is disposed between the ring of expandable struts of the plurality of expandable struts and the distal-most expandable struts of the plurality of expandable struts.

7. The device of claim 1, wherein the peaks of the proximal-most expandable struts comprise an eyelet.

8. The device of claim 1, wherein the plurality of longitudinal struts comprise six longitudinal struts and wherein the plurality of expandable struts comprises eighteen expandable struts.

9. The device of claim 1, wherein the distal-most expandable struts of the plurality of expandable struts at the distal portion of the frame each comprise an anchor having a tissue penetrating portion with a sharp tip configured to penetrate tissue of the blood vessel to anchor the frame within the blood vessel.

10. The device of claim 9, wherein the sharp tip of the tissue penetrating portion of each anchor is configured to penetrate a graft disposed within the blood vessel to secure the graft to the blood vessel.

11. The device of claim 9, wherein each anchor is attached to each of the distal-most expandable struts via a support frame.

12. The device of claim 9, wherein each anchor comprises at least two prongs configured to transition between a restrained state where the at least two prongs are juxtaposed and an unrestrained state where the at least two prongs are deflected away from each other.

13. The device of claim 12, wherein each anchor comprises a sleeve slidably disposed over the at least two prongs, the sleeve configured to move from a first position where the at least two prongs are in the restrained state and a second position where the at least two prongs are permitted to transition to the unrestrained state.

14. The device of claim 13, wherein each anchor comprises:
   a distal stop configured to prevent movement of the sleeve distally beyond the distal stop; and
   a proximal stop configured to prevent movement of the sleeve proximally beyond the proximal stop, wherein, upon application of at least a predetermined force to the sleeve, the anchor is configured to contract inward to permit the sleeve to move proximally beyond the proximal stop.

15. The device of claim 12, wherein the at least two prongs comprise two external prongs and two internal prongs.

16. The device of claim 15, wherein, in the unrestrained state, a first pair of external and internal prongs is configured to deflect away from a second pair of external and internal prongs.

17. The device of claim 16, wherein at least one pair of juxtaposed prongs of the at least two prongs comprises a buckling prevention lock.

18. The device of claim 17, wherein the buckling prevention lock comprises:

a protrusion extending from a first prong of the at least one pair of juxtaposed prongs; and a recess formed in a second prong of the at least one pair of juxtaposed prongs, wherein, in the restrained state, the recess is configured to receive the protrusion therein to provide friction and prevent buckling of the anchor as the at least one pair of juxtaposed prongs transitions from the restrained state to the unrestrained state.

19. The device of claim 17, wherein the buckling prevention lock is disposed on a middle region of the at least one pair of juxtaposed prongs.

20. The device of claim 17, wherein the at least one pair of juxtaposed prongs comprises the two internal prongs.

21. The device of claim 17, wherein the at least one pair of juxtaposed prongs comprises at least one of the first pair of external and internal prongs or the second pair of external and internal prongs.

22. A system for delivering and deploying a tissue anchoring device within the blood vessel, the system comprising;

the tissue anchoring device of claim 1;

a dual balloon catheter comprising:

an elongated shaft;

a locking balloon disposed on a distal region of the elongated shaft, the inflatable locking balloon configured to be inflated to contact at least a proximal portion of the tissue anchoring device to prevent movement of the tissue anchoring device relative to the blood vessel; and an activation balloon disposed on the distal region of the elongated shaft distal to the locking balloon, the activation balloon configured to be inflated to apply a radially outward force to expand at least a distal portion of the tissue anchoring device and cause one or more anchors of the tissue anchoring device to penetrate the blood vessel, wherein a distal end of the locking balloon is coupled to the elongated shaft in a manner such that, when the locking balloon is inflated, a distal portion of the locking balloon is inverted within itself.

23. The system of claim 22, wherein the activation balloon comprises a foldable internal balloon and an expandable outer sleeve disposed over the foldable internal balloon, the expandable outer sleeve configured to prevent puncturing of the foldable internal balloon as the foldable internal balloon is inflated within the blood vessel.

24. The system of claim 22, further comprising a delivery catheter comprising:

an elongated shaft having a distal end comprising a nose cone;

a retractable sheath configured to releasably engage the nose cone, the sheath configured to receive the tissue anchoring device therein in the collapsed configuration; and a holder slidably disposed within the sheath, the holder comprising a plurality of recesses configured to releasably engage a plurality of eyelets disposed on the proximal portion of the tissue anchoring device, wherein movement of the nose cone distally relative to the sheath exposes the distal portion of the tissue anchoring device, such that the distal portion of the tissue anchoring device transitions from the collapsed configuration to a partially expanded configuration, and wherein movement of the sheath proximally relative to the nose cone exposes the proximal portion of the tissue anchoring device, such that the proximal portion of the tissue anchoring device transitions from the collapsed configuration to a fully expanded configuration for the full deployment.

25. A method of securing a graft to a tissue comprising:

collapsing the tissue anchoring device of claim 1 within a delivery catheter;

partially releasing the tissue anchoring device from the delivery catheter in a blood vessel such that the distal portion and the ring of expandable struts transition to the expanded configuration such that the ring of expandable struts of the plurality of expandable struts contacts a graft positioned within the blood vessel to thereby stabilize the frame within the graft;

fully releasing the tissue anchoring device from the delivery catheter such that the ring of expandable struts contacting the graft stabilize the frame during full deployment as the proximal portion transitions from the collapsed configuration to the expanded configuration; and removing the delivery catheter from the blood vessel.

26. The method of claim 25, wherein the distal-most expandable struts of the plurality of expandable struts at the distal portion of the frame each comprise an anchor having a tissue penetrating portion.

27. The method of claim 26, further comprising driving the tissue penetrating portion of each anchor through the graft and the blood vessel.

28. The method of claim 27, wherein driving the tissue penetrating portion of each anchor through the graft and the blood vessel comprises inflating an activation balloon of a balloon catheter within at least a distal portion of the tissue anchoring device.

29. The method of claim 28, further comprising:

inflating a locking balloon of the balloon catheter within at least a proximal portion of the tissue anchoring device to secure the tissue anchoring device within the blood vessel during inflation of the activation balloon, wherein the locking balloon is proximal to the activation balloon.

* * * * *